United States Patent [19]

Schlawne et al.

[11] Patent Number: 5,679,898
[45] Date of Patent: Oct. 21, 1997

[54] PROCESS AND DEVICE FOR DETECTING FLAWS ON STRETCHED WORKPIECES, ESPECIALLY TUBES AND BARS

[75] Inventors: Friedhelm Schlawne, Duisburg; Heinz Schneider, Düsseldorf, both of Germany

[73] Assignee: Mannesmann Aktiengesellschaft, Dusseldorf, Germany

[21] Appl. No.: 627,938

[22] Filed: Mar. 28, 1996

[30] Foreign Application Priority Data

Mar. 31, 1995 [DE] Germany ............ 195 13 194

[51] Int. Cl.$^6$ ............... G01N 29/04
[52] U.S. Cl. ............... 73/622; 73/638; 73/641
[58] Field of Search ............... 73/622, 625, 632, 73/637, 638, 641, 643, 600

[56] References Cited

U.S. PATENT DOCUMENTS 3,828,609  8/1974  Furon ............... 73/622
4,099,418  7/1978  Bennett ............... 73/641

FOREIGN PATENT DOCUMENTS 2027199  2/1980  United Kingdom ............... 73/622

*Primary Examiner*—Christine K. Oda
*Attorney, Agent, or Firm*—Cohen, Pontani Lieberman & Pavane

[57] ABSTRACT

A process for detecting flaws on stretched workpieces, especially tubes and bars, in which the test specimen is passed in the axial direction and without rotation by fixed electrodynamic transducers arranged separately in the peripheral direction. Wave pulses travelling in both peripheral directions are generated in the test specimen at different locations in alternating fashion in the test cycle, and the location of reception for the reflection signals is different from that for the transmission signals. The wave pulses travelling in both directions are generated at at least four locations separated symmetrically from one another in the peripheral direction in alternating fashion in the test cycle. Each particular sequence of reception signals is evaluated separately, and for each cycle the reception signal and a burst signal are fed to a peak detector and the output signal of the peak detector is transmitted in digital form to a computer. The device for carrying out the process includes electrodynamic transducers, which have separate transmitting and receiving coils, and lie on a peripheral plane, and are staggered around the perimeter of the test specimens. The transducers are arranged in a fixed manner, and are connected to an analysis unit. The device calls for 2·n transducers, where n>2, arranged symmetrically around the perimeter, whereby every two transducers are placed together on one transducer carrier and the spacing of the transducer carriers is 360°/n. Furthermore, each transducer has its own local electronics system and its own analysis channel.

8 Claims, 5 Drawing Sheets

S : TRANSMISSION COIL OF TRANSDUCER

SV : TRANSMISSION AMPLIFIER

SM : TRANSMISSION AMPLIFIER  } COMPUTER CONTROLLED
SG : SIGNAL SOURCE

- E : RECEIVING COIL OF TRANSDUCER
- VV : PREAMPLIFIER
- V : INTEGRADED AMPLIFIER

- HV : MAIN AMPLIFIER
- MX : MULTIPLEXER
- PD : PEAK DETECTOR
- BG : APERTURE GENERATOR
- AD : ANALOG/DIGITAL CONVERTER
- R : PRECOMPRESSION CALCULATOR

} CONTROLLED BY CENTRAL COMPUTER

PROCESS AND DEVICE FOR DETECTING FLAWS ON STRETCHED WORKPIECES, ESPECIALLY TUBES AND BARS

BACKGROUND OF THE INVENTION

1. Field of the Invention

The invention relates to a process for detecting flaws on stretched workpieces, especially tubes and bars.

2. Description of the Prior Art

From DE 39 43 226 B1, a generic process is known in which a test specimen is passed axially by at least one fixed electrodynamic transducer without being turned. Tangentially rotating wave pulses, which propagate in both peripheral directions, are cyclically generated in the test specimen and are received at a receiving location that is shifted relative to the transmitting location by one-quarter of the trace wavelength of the conducted waves. The location of reception and of excitation of the wave pulses, which travel simultaneously in both peripheral directions of the test specimen, is selected so that the two wave pulses, travelling without disturbance, interfere destructively at the location of the receiver. For each cycle, the received signal and a burst signal which has a large pulse-duty factor, are fed to a peak detector, and the output signal of the peak detector is sent in digital form to a computer. The period of the burst signal is selected to be less than one-fourth of the period of the wave pulse around the test specimen and the length of the burst signal corresponds to the decay time of wave pulses travelling undisturbed in a flawless workpiece.

This known process has the disadvantage of not being suitable for tubes with a large circumference, i.e., a diameter >400 mm. In addition, no information is provided about the circumferential or perimeter coordinates of the defect. This is not acceptable for welded tubes that will be repaired.

SUMMARY OF THE INVENTION

The object of the present invention is to provide a process for detecting flaws on stretched workpieces, especially tubes and bars, which is suitable for tubes with a diameter >400 mm and, in particular, for large tubes with a diameter >900 mm and with which the perimeter coordinates of the defect can be determined. It is a further object to provide a structurally simple and economical device which carries out the process.

Pursuant to this object, and others which will become apparent hereafter, one aspect of the present invention resides in a process in which wave pulses travelling in both peripheral directions are generated at a minimum of four locations arranged symmetrically separated in the peripheral direction, whereby in each test cycle, in alternating fashion, half of the total number of excitation locations are triggered. This means that it is also possible to have six or even eight separate generating locations. As generating locations are added, however, the cost of controlling the overall apparatus electronically and mechanically increases.

The selected arrangement has the following advantages: Before a new test-shot is carried out, the sound of the previous test-shot must die down completely. In order to achieve the highest possible clock rate and thus good testing output, half of the total number of transducer (i.e., when there are six transducers: three transducers) are triggered simultaneously. This ensures that the entire tube perimeter is tested in overlapping fashion after a total of two test-shots. The symmetrical arrangement selected results in the lowest possible mutual interference between reflection signals and transmission signals and guarantees regular distances between the transmission peaks. In addition, the symmetrical arrangement guarantees optimal overlapping of the tested areas.

In the reflection technique, processing the accumulated quantity of data is particularly important. An aperture generator produces a square-wave signal with a typical period of 33 µs and a pulse-duty factor of 99:1. The total length of the square-wave signal (burst signal) is thereby adjusted, dependent on diameter, to the signal length to be analyzed. For example, for a tube with a diameter of 1 meter, 34 apertures are used. This corresponds, as seen in the peripheral direction, to a raster of 50 mm. For normal testing jobs, this raster is sufficient, because the contact point always becomes several centimeters in size and adjacent regions are therefore included along with it. In special cases, it may be necessary to reduce the raster to 20 mm. To ensure that only truly interesting signals are processed, the central computer is sent only amplitude values clearly above, for example, 6 dB of the noise level, together with the number of the aperture (i.e., the propagation time). Because the number of the aperture into which the reflection display has fallen is known, it is possible to know the distance of the possible defect from the combined transducer in question. However, it is not yet possible to decide whether the defect is located in the clockwise or the counter-clockwise direction, as seen from the transducer. To do this, the reflection signal of another transducer must also be considered by a suitable logic, so that it becomes possible to determine in which peripheral segment the defect lies. After the test procedure is concluded, the data can be analyzed using suitable statistical suppressor algorithms, e.g., individual displays will be eliminated on the basis of statistical disturbers. Only when two transducers in the same area detect a display is a defect to be assumed. Then, for a defect thus delineated, the amplitude values are also available, so that evaluation as an error to be reported can be made.

The advantage of the described procedure is, firstly, that the quantity of data to be processed by the central computer is reduced in advance by the type of aperture setting and, secondly, that the perimeter coordinates of the defect can be determined. In the case of precision tubes, for example, determining the perimeter coordinates of the defect is unimportant, because once a set defect level is exceeded, the tube in question must be rejected. Local repair is not possible and would, at any rate, be much too expensive. However, in the case of large tubes, the possibility of repair plays an important roll. In this connection, in respect to welded large tubes, the following point must be taken into account. By conveying the test specimens to the unit in a controlled manner, it must be ensured that the weld seam does not lie below a transducer. Were this to happen, this transducer would then have an undefined and inadequate coupling. The weld seam causes small reflection displays, which are to be expected over more or less the entire length of the tube. This line can be recognized and associated with the seam.

The simultaneous use of the reflection technique according to the invention and the ultrasonic irradiation known per se has the advantage that defects which vary widely in shape and size can be reliably detected. For example, using the reflection technique, it is almost impossible to reliably detect scars that run flatly on the surface. However, these are detected by the ultrasonic technique.

The simple and economical mechanical construction of the inventive device for carrying out the above-discussed process is particularly advantageous. In each case, two transducers are placed together on one transducer carrier. The transducer carrier can be moved as a whole on an axis through the centerpoint of the tube and can carry out a slight turning movement around the identified axis. In this way, any shifting of the tube during the test is compensated for, and the mechanism can be very simply designed, particularly with respect to establishing its dimensions.

Expressed in general terms, according to the invention, 2·n transducers, wherein n>2 are placed at the circumference of the test piece so that the spacing of the transducers on a transducer carrier equals 360°/4/n. The spacing of the transducer carriers, each of which includes two transducers, is 360°/n.

The inventive process is also suitable for the interior testing of tubes, insofar as the inner diameter permits passage of the mechanical structure. The simple design resulting from the invention is thereby advantageous.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
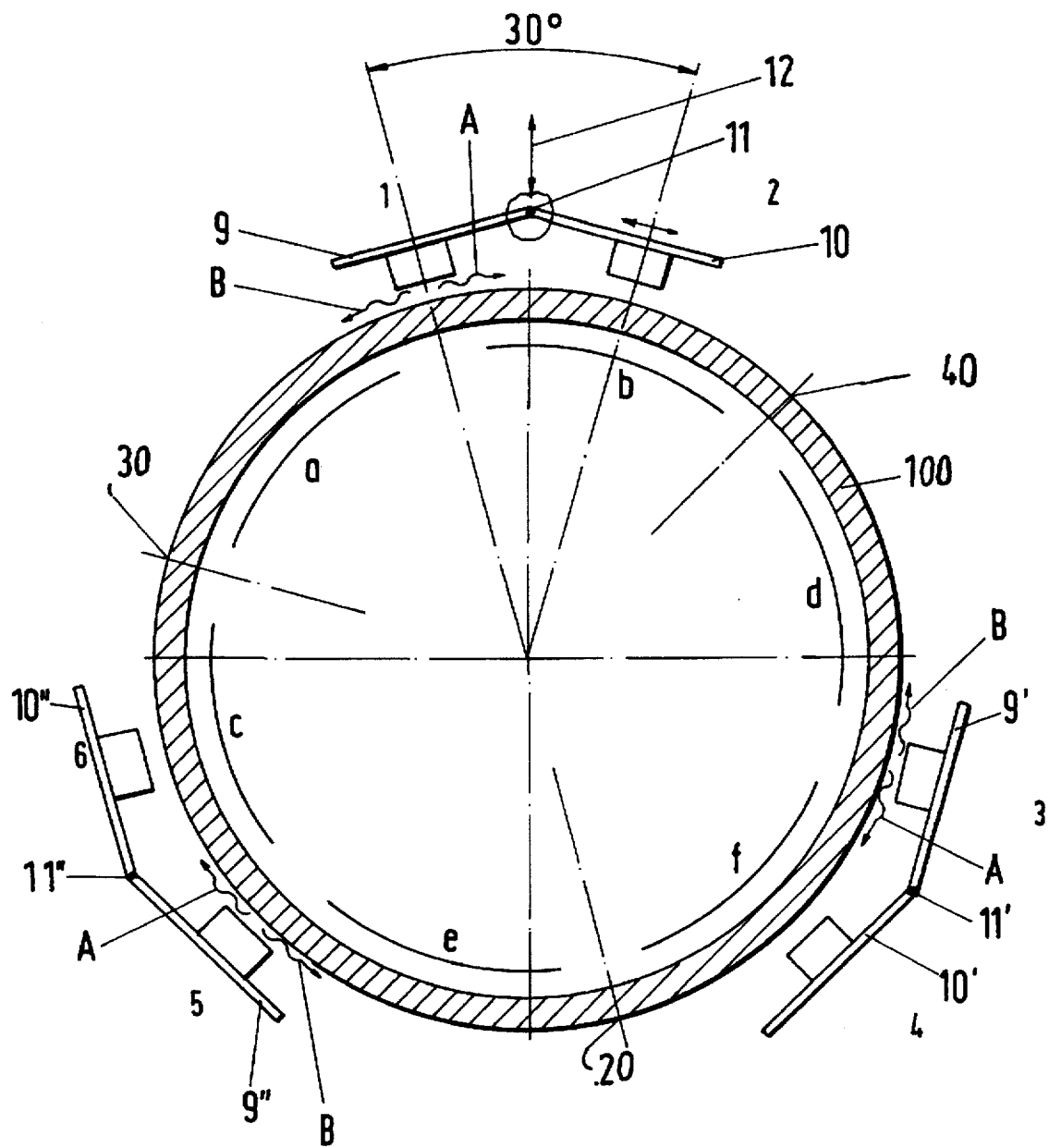
FIG. 1 is a schematic diagram for implementing the process according to the invention.

FIG. 1 shows the schematic arrangement for implementing the process according to the invention. Of the total of six transducers 1 to 6 arranged at a slight distance from the test specimen 100, three (here, transducers 1, 3, 5) simultaneously emit a wave pulse A, B in the two circumferential directions of the test specimen 100. In this example, the emitted wave pulse A, B is characterized by a wave line, and it has been established that A should be the wave pulse emitted in the clockwise direction and B that emitted in the counterclockwise direction. Both wave pulses A, B travel around several times in the circumferential direction and meet again at two defined points on the circumference. One point is at each transducer itself, i.e., at transducers 1, 3, 5, and the other point is on the exactly opposite side, shifted by 180°, marked here as positions 20, 30, 40. The transducers 1 to 6 used here are called combined transducers, because they have both transmitting and receiving windings. To ensure the necessary testing sensitivity, the reflection technique is used primarily, i.e., portions of waves reflected at a defect are detected. In addition, transmission signals are also measured and evaluated.

In the case of large tubes, i.e., tubes with diameters >900 mm, it is necessary, in order to monitor the entire circumference of the test specimen without gaps, to use the combined transducers 1 to 6. These six transducers 1 to 6 are arranged on a plane on the circumference at the positions minus 15°, 15° (transducers 1, 2), 105°, 135° (transducers 3, 4) and 225°, 255° (transducers 5, 6). Three transmitting transducers (1, 3, 5) or (2, 4, 6) are simultaneously triggered in each case.

Figure 2:
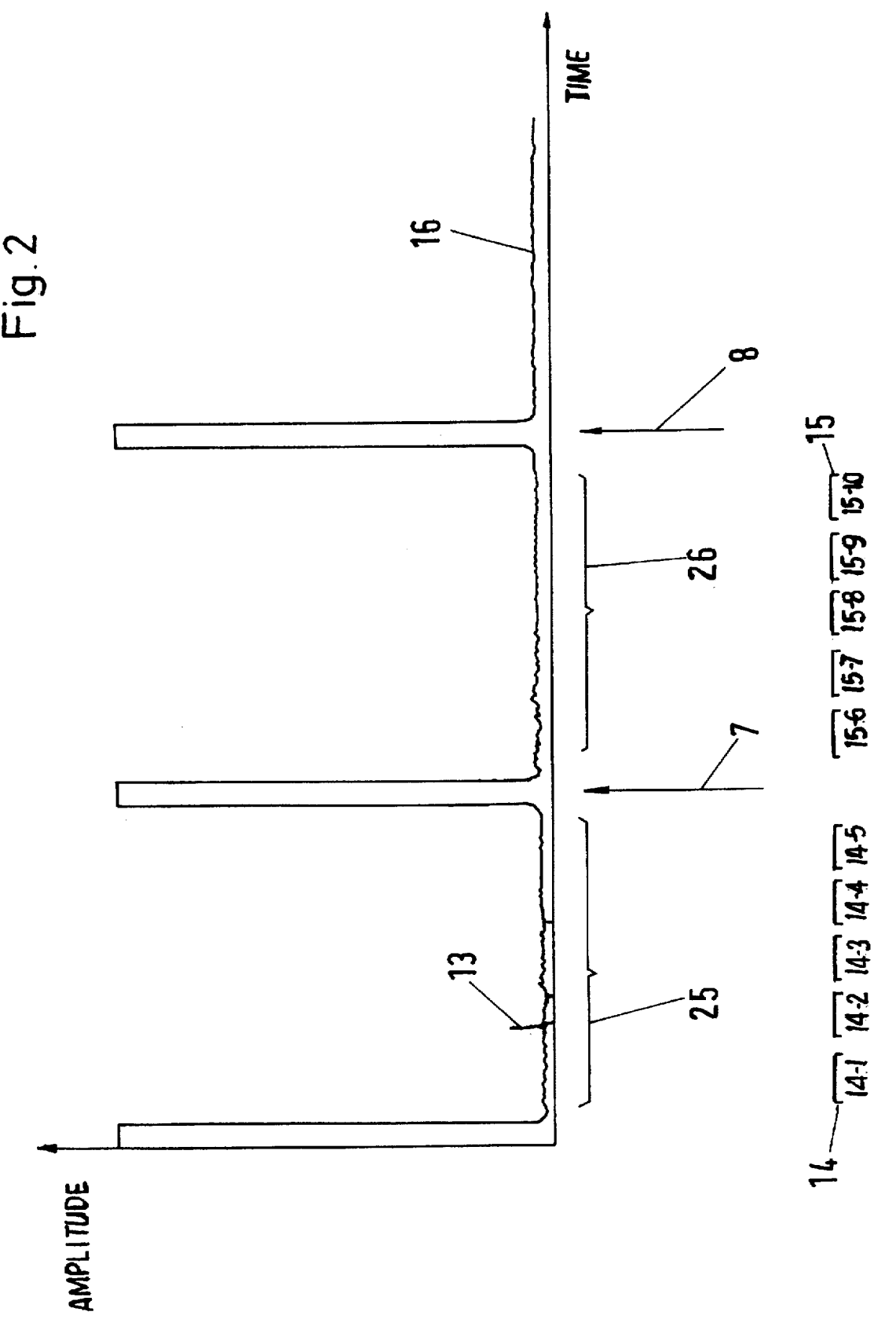
FIG. 2 schematically illustrates the received signal of the transducer with triggered transmitting transducers.

According to the invention, two transducers, i.e., transducers 1, 2; transducers 3, 4; or transducers 5, 6 are always arranged on one transducer carrier. The transducer carrier consists of two holders 9, 10; 9',10'; 9", 10" which can be rotated around a point 11; 11'; 11". The double arrow 12 in the area of the transducers 1, 2 indicates the possible movement of the transducer carrier. In this way, a simple adjustment to different dimensions is possible. To explain the process, let us consider, for example, the transducer 1 in a timed cycle I. FIG. 2 shows, in schematic fashion, a received signal. No reflection signals can be received directly below the transducer, because of the cross-talk of the transmitting and receiving windings. After the amplifier override has decayed, reflection signals are received from the indicated Sections a, b (FIG. 1). This corresponds to section 25 in FIG. 2. Because the transducers 3, 5 are arranged symmetrically relative to the transducer 1, the waves emitted by the transducers 3, 5 arrive at the transducer 1 at practically the same time and, due to their great amplitude, cause an override of the reception amplifier of the transducer 1. Because we must assume an undefined superimposition of the two wave trains, it is not useful to conduct an amplitude measurement in this time period. Reflection signals follow from sections c and d (FIG. 1), upon which the waves emitted by the transducers 3 and 5 in the other respective peripheral direction arrive simultaneously at the transducer 1. This corresponds to section 26 in FIG. 2. A measurement in a longer time interval, i.e., signals from sections e, f (FIG. 1), is not useful, because the ordering of individual displays becomes increasingly complicated and because the reflection displays, due to the sound damping, have amplitudes that are too small. However, it must be noted that another test shot cannot take place until the sound has completely "died down," i.e., the amplitude of the rotating wave disappears in noise. The received signals of the transducers 3, 5 have an analogous structure. Because each perimeter segment a to f is thus tested twice, it is, in principle, possible to decide where a reflection display comes from, since the transducers 1 to 6 do work bi-directionally. For complete monitoring of the entire perimeter, the analogous procedure is followed with the transducers 2, 4, 6 in the subsequent timed cycle II. It is thereby assumed, in the case of each of the border regions of the monitored segments, that these have already been monitored in timed cycle I, because generally the sections that cannot be tested in one cycle are smaller than those that can be tested.

Along with the reflection signals, transmission signals can also be received in each cycle. Relative to the transducer 1, the second amplitude 7 in FIG. 2 shows the transmitted signals of the transducers 3, 5, for example, in the direction A, while the third amplitude 8 in FIG. 2 shows the transmitted signals of the transducers 3, 5 in the opposite direction B.

To explain how the perimeter coordinates are found, section 25 in FIG. 2 shows the amplitude 13 of a defect. The apertures 14 and 15 set in the respective sections 25 and 26 are entered schematically below the screen display. As an example, 5 apertures are drawn per section; in reality, these are much closer to each other. Ordering now occurs in such a way that the peak detector detects the amplitude 13 rising above the noise background 16 and stores the maximum measured amplitude value. At the same time, the number of the set aperture is counted. In this case, counting from the left, it is aperture No. 14-2 of aperture 14. Because the aperture number corresponds to a propagation time, it is now simple to calculate the distance in mm of the defect 13 from the transducer 1. If, when the next test shot of the transducers 2, 4, 6 is carried out, this defect 13 is once again detected by one of the transducers 2, 4, 6, then we have, first of all, confirmation that this is not a matter of statistical interference; and secondly, by logically interconnecting the two propagation times, it is possible to precisely establish the perimeter coordinates of the defect 13. In the case of seamless tubes, the ordering of the transducer pairs 1,2; 3,4; 5,6 relative to the real-time position of the test specimen is carried out by means of a previously drawn pilot line; in the case of welded tubes, the weld seam usually performs this function.

Figure 3:
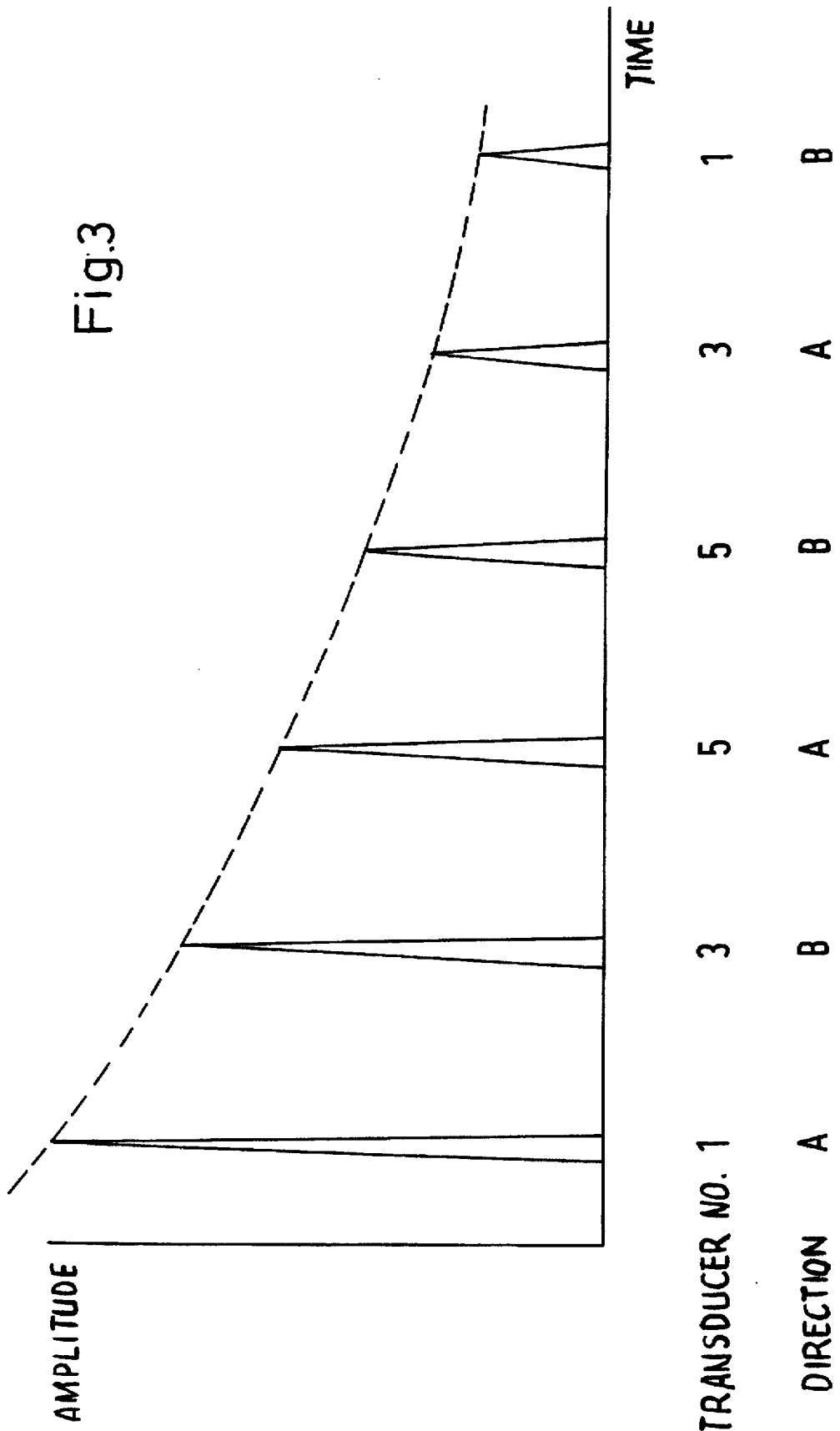
FIG. 3 schematically illustrates the received signal of the transducer with triggered transducers.

FIG. 3 schematically shows the received signal from the transducer 2 in the cycle I. In this cycle I, the transducers 1, 3, 5 are triggered. As already established in FIG. 1, direction A means that the sound travels in the clockwise direction and direction B counterclockwise, in relation to FIG. 1. The chronological distance of the received signals of the sound waves, which arrive from the three transmitter transducers activated in time, is equidistant, due to the selected symmetry of the testing head arrangement. In order to avoid an override of the transmitted signals, the amplification factor is clearly smaller than when reflection signals are received. Transmitted signals with the same structure as the transducer 2 are received at the same time by the receivers of the transducers 4 and 6.

In the second timed cycle II, the transducers 2, 4, 6 are triggered and the transducers 1, 3, 5 register the transmitted signals. The test shown is carried out during the longitudinal transport of the test specimen 100, whereby the linear speed is greater than 10 m/min. During the test, no rotation of the test specimen 100 or mechanical scanning of the surface of the test specimen 100 with the transducers is necessary.

Figure 5:
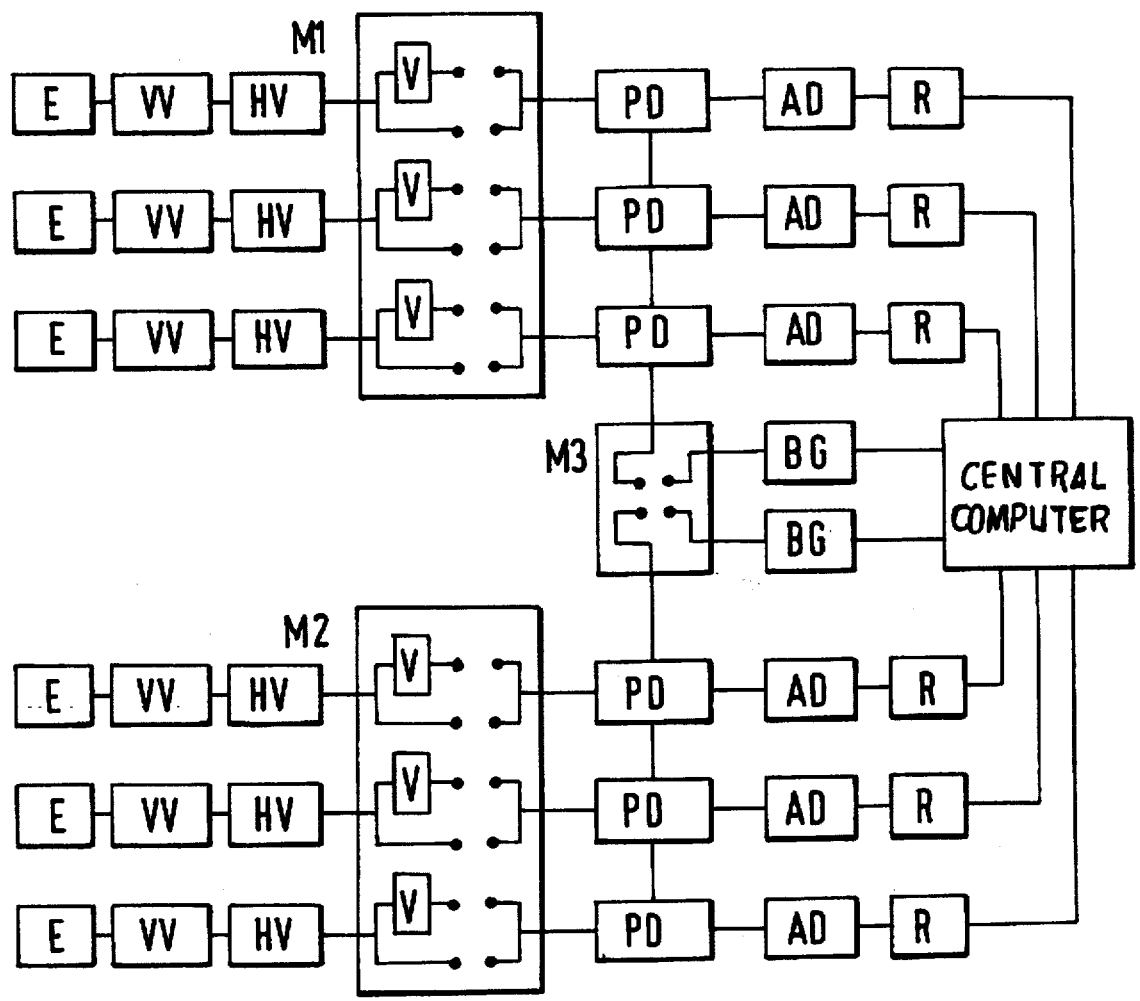
FIG. 5 is a block diagram of the receiver side of the inventive device.

In respect to electronics, each of the six combined electrodynamic transducers 1 to 6 has its own local electronics system and its own analysis channel. Each local electronics system contains a four-channel transmission amplifier V and a low-noise pre-amplifier VV for the received signals of the combined transducers 1 to 6 (FIG. 5). The cable length between one transducer and its associated local electronics system is usually short, for reasons of damping.

Figure 4:
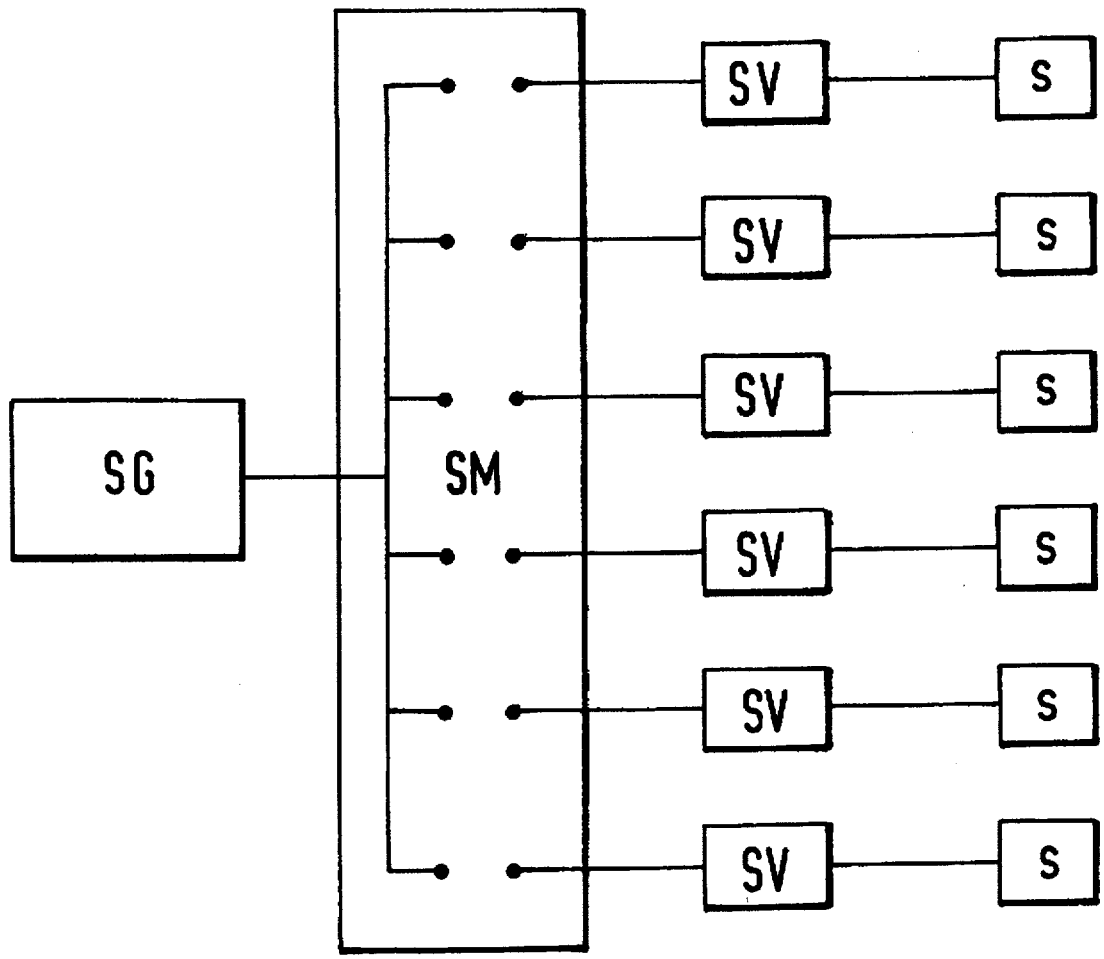
FIG. 4 is a block diagram of the transmitter side of the inventive device.

On the transmission side, a signal source (burst generator) SG triggered by the central computer is used, which produces a burst signal for controlling the transmission amplifier (FIG. 4). The signal from the signal source SG is sent to a multiplexer SM where the signal is split into six paths. Each path includes an amplifier SV and a sending coil S of one of the transducers 1–6. In each test cycle, the three transmission electronics systems are operated in parallel fashion via the multiplexer, and thus the transducers are controlled with the same burst signal. The signals are received by the receiving coils E of the transducers 1–6, are pre-amplified by preamplifiers VV, and are fed into the electronic analysis system (see FIG. 5). To begin with, each analysis channel contains a computer-replaceable main amplifier HV, so as to be able to set a suitable signal level. Each receiver transducer is used, in alternating fashion, to receive reflection signals and to measure transmission signals. In two multiplexers M1, M2 with three outputs each, there are integrated amplifiers V with a fixed amplification value, to permit quick switch over (timing-wise) from high amplification to low amplification.

The total surface of the test specimen is to be tested using as high a timing rate as possible, in order to permit rapid testing and also to ensure as reliable a test as possible. This requires a drastic reduction in the quantity of data accumulated, especially using the reflection technique. The signals to be processed are reduced, firstly, by sending to the central computer only amplitude values that are clearly above the noise level and, secondly, by designing the burst signal (aperture) so that it results, depending on the testing job, in the required site resolution. This is accomplished by the signals from the multiplexers M1, M2 being sent to peak detectors PD. The signals from the peak detectors PD are sent to a third multiplexer M3 which furthers the signals to the central computer via aperture generators BG. The peak detector signals are also sent to the computer via analog-digital converters AD and precompression calculators R to reduce or compress the signals before reaching the computer.

The invention is not limited by the embodiments described above which are presented as examples only but can be modified in various ways within the scope of protection defined by the appended patent claims.

We claim:

1. A process for detecting flaws on stretched workpieces, comprising the steps of:

passing a test specimen in an axial direction and without rotation by fixed electrodynamic transducers arranged separately and peripherally about the test specimen; generating and transmitting wave pulses that travel in both peripheral directions at different locations in the test specimen in an alternating fashion during a test cycle at at least four locations symmetrically separated in the peripheral direction; receiving reflection signals and transmission signals at different locations; evaluating each particular sequence of received signals separately; feeding the received signals and a burst signal to a peak detector; transmitting an output signal of the peak detector in digital form to a computer, so that during the test cycle, in an alternating fashion, half a total number of excitation locations are triggered, and the receiving of the transmission signals occurs at a lower amplification compared to the receiving of the reflection signals; configuring the burst signal for measuring the reflection signals so that a required site resolution results; and further processing only amplitude values above a preselected distance between an amplitude value and a noise level measured in an aperture.

2. A process as defined in claim 1, wherein the step of generating wave pulses includes generating wave pulses travelling in both peripheral directions at six circumferential locations in alternating fashion in the test cycle.

3. A process as defined in claim 1, further including selecting a period for the burst signal for measurement of the reflection signals so that the period corresponds to a required site resolution in the peripheral direction of no more than 5 cm.

4. A process as defined in claim 1, and further comprising the step of interconnecting reflection waves caused by a defect that are displayed in at least two transducers to one another by means of a logic circuit in the computer to determine the perimeter coordinates of the defect.

5. A device for detecting flaws on a stretched workpiece test specimen having a diameter greater than 400 mm, comprising: 2·n electrodynamic transducers, with n>2, having separate transmitting and receiving coils lying on a peripheral plane and arranged in a symmetrically staggered fashion around a perimeter of the test specimen; analysis means connected to the transducers for analyzing signals from the transducers; a plurality of transducer carriers, two of the transducers being arranged on each one of said transducer carriers, the transducer carriers being spaced 360°/n; and a plurality of local electronic system means and analysis channel means, one of the plurality of electronic system means and analysis channel means being respectfully connected to each of the 2–n electrodynamic transducers for processing signals, the plurality of electronic system means being operative to trigger all the transmitting coils simultaneously.

6. A device as defined in claim 5, wherein the two transducers arranged on said each one of said transducer carriers are spaced based on 360°/4/n.

7. A device as defined in claim 5, wherein each of the transducers is separated from its associated local electronic means by as short a distance as possible.

8. A device for detecting flaws on a stretched workpiece test specimen, comprising: 2·n electrodynamic transducers, with n>2, having separate transmitting and receiving coils lying on a peripheral plane and arranged in a symmetrically staggered fashion around a perimeter of the test specimen; analysis means connected to the transducers for analyzing signals from the transducers; a plurality of transducer carriers, two of the transducers being arranged on each one of said transducer carriers, the transducer carriers being spaced 360°/n; and local electronic system means and analysis channel means for each transducer for processing signals, said each one of said transducer carriers including two separate holders, one of the two transducers being arranged on a respective one of the holders, the holders being connected together at a rotation point that lies between the two transducers so that the holders can rotate about the rotation point.

* * * * *